(12) United States Patent
Shimomura

(10) Patent No.: US 8,765,480 B2
(45) Date of Patent: Jul. 1, 2014

(54) METHOD FOR RECOVERING METAL AND KIT FOR RECOVERY OF METAL FOR USE IN THE SAME

(75) Inventor: Yuka Shimomura, Kyoto (JP)

(73) Assignee: ARKRAY, Inc., Kyoto (JP)

(*) Notice: Subject to any disclaimer, the term of this patent is extended or adjusted under 35 U.S.C. 154(b) by 0 days.

(21) Appl. No.: 13/437,279

(22) Filed: Apr. 2, 2012

(65) Prior Publication Data

US 2012/0251390 A1 Oct. 4, 2012

Related U.S. Application Data

(60) Provisional application No. 61/533,073, filed on Sep. 9, 2011, provisional application No. 61/533,121, filed on Sep. 9, 2011, provisional application No. 61/538,755, filed on Sep. 23, 2011, provisional application No. 61/538,766, filed on Sep. 23, 2011.

(30) Foreign Application Priority Data

| Apr. 4, 2011 | (JP) | ................................ | 2011-083024 |
| Jun. 21, 2011 | (JP) | ................................ | 2011-136921 |
| Sep. 22, 2011 | (JP) | ................................ | 2011-207907 |
| Sep. 22, 2011 | (JP) | ................................ | 2011-207908 |
| Mar. 16, 2012 | (JP) | ................................ | 2012-060102 |

(51) Int. Cl.
| G01N 33/20 | (2006.01) |
| G01N 15/06 | (2006.01) |
| G01N 33/00 | (2006.01) |
| C07C 245/00 | (2006.01) |
| C07C 337/00 | (2006.01) |
| C22B 3/00 | (2006.01) |
| C01G 55/00 | (2006.01) |
| C22B 11/00 | (2006.01) |
| B01D 11/00 | (2006.01) |
| B01F 1/00 | (2006.01) |

(52) U.S. Cl.
USPC ................ 436/73; 422/68.1; 436/74; 436/80; 436/81; 436/84; 436/77; 534/562; 564/19; 423/1; 423/22; 423/658.5

(58) Field of Classification Search
USPC ..................... 436/73, 81, 84, 80, 77
See application file for complete search history.

(56) References Cited

U.S. PATENT DOCUMENTS

| 4,876,068 A | 10/1989 | Castaneda |
| 4,920,057 A | 4/1990 | Castaneda |
| 4,950,408 A * | 8/1990 | Duisters et al. ................ 210/660 |
| 2011/0020943 A1 | 1/2011 | Okamoto et al. |

FOREIGN PATENT DOCUMENTS

| EP | 0319615 A1 | 6/1989 |
| EP | 0536059 A2 | 4/1993 |
| JP | 58-049490 A | 3/1983 |
| JP | 63-067529 B | 12/1988 |
| JP | 2-034655 B | 8/1990 |
| JP | 5-232028 A | 9/1993 |
| JP | 2569157 B2 | 1/1997 |
| JP | 9-047768 A | 2/1997 |
| JP | 10-113677 A | 5/1998 |
| JP | 11-042469 A | 2/1999 |
| JP | 2969226 B2 | 8/1999 |
| JP | 2969226 B2 | 11/1999 |
| JP | 2000-136371 A | 5/2000 |
| JP | 2003-194798 A | 7/2003 |
| JP | 2009-294024 A | 12/2009 |
| JP | 2009-294060 A | 12/2009 |
| WO | 2009/116669 A1 | 9/2009 |

OTHER PUBLICATIONS

Andoh et al., "Solid Phase Extraction of Ni and Cd by Chelating Cellulose Functionalized with Thiolactic Acid," Bunseki Kagaku, 57: 1027-1032 (2008).
Hayashi et al., "Study on Quantitative Analysis of Heavy Metals in Waste Water by Chelating resin disk preconcentration/ICP-AES," Annual Report of the Kawasaki Municipal Research Institute for Environmental Protection 45-50 (2003).
Itoh et al., "Determination of Trace Metals in Coastal Seawater around Okinawa and Its Multielement Profiling Analysis," Bunseki Kagaku, 58: 257-263 (2009).
Matsunaga, "Recognition, separation and concentration of metal ions with chelating resins or chelating reagent impregnated resins (Review)," Bunseki Kagaku, 50: 89-106 (2000).
Nagai et al., "The precipitation chromatography of several metal cations with thiooxine impregnated filter paper," Bunseki Kagaku, 24: 184-187 (1975).
Oikawa et al. "Preconcentration of Heavy Metal Ions with Thermo-Sensitive Chitosan and Atomic Absorption Spectrometric Determination of Trace Cadmium in Water," Bunseki Kagaku, 56: 721-728 (2007).
Sakamoto et al., "Pretreatment Method for Determination of Trace Elements in Seawater Using Solid Phase Extraction Column Packed with Polyamino-Polycarboxylic Acid Type Chelating Resin," Bunseki Kagaku, 55: 133-139 (2006).

(Continued)

*Primary Examiner* — Jill Warden
*Assistant Examiner* — Julie Tavares
(74) *Attorney, Agent, or Firm* — Morgan, Lewis & Bockius LLP

(57) ABSTRACT

A method for recovering a metal, capable of recovering a metal easily without requiring the use of an organic medium, is provided. A first complex between a first chelating agent and a metal present in a sample is formed in a first mixture prepared by mixing the first chelating agent and the sample. Then, the first complex is recovered from the first mixture, and a second complex between the metal derived from the first complex and a second chelating agent is formed in a second mixture prepared by mixing the first complex and an aqueous solution of the second chelating agent. The aqueous solution is under the pH conditions where the first chelating agent can be insoluble in the aqueous solution. Then, a liquid fraction containing the second complex is recovered from the second mixture. Thus, the metal can be recovered.

11 Claims, No Drawings

(56) References Cited

OTHER PUBLICATIONS

Shamsipur et al., "Solid phase extraction and determination of sub-ppb levels of hazardous Hg2+ions," Journal of Hazardous Materials B117, 129-133 (2005).

Takeuchi et al., "An Accurate and Rapid Analysis for Lead in Urine Using Solid Phase Extraction Column Packed with a Functional Chelating Resin," Japanese Journal of Occupational Medicine and Traumatology, 55: 15-19 (2007).

Ueno et al., "Bismuthiol II," Handbook of Organic Analytical Reagents, CRC Press, 479-485 (1992).

Ueno et al., "Dithizone and Related Agents," Handbook of Organic Analytical Reagents, CRC Press, 431-443 (1992).

Ueno et al., "Thiothenoyltrifluoroacetone," Handbook of Organic Analytical Reagents, CRC Press, 487-492 (1992).

Ueno et al., "Thioxine," Handbook of Organic Analytical Reagents, CRC Press, 445-456 (1992).

Watanabe et al., "Spectrophotometric Determination of Small Amounts of Cadmium(II) Using Formation of Zinc(II) Complex with Anionic Porphyrin as an Indicator Reaction," Bunseki Kagaku, 59: 589-595 (2010).

Yamada et al., "Simultaneous determinations of Cu, Cd and Pb in river-water samples by multielement isotope dilution/ICP-MS with the aid of chelating resin preconcentration," Bunseki Kagaku, 50: 433-439 (2001).

Yamamoto et al., "Highly Efficient and Automatic Collection/Concentration with Chelating Resin for Inductively Coupled Plasma Atomic Emission Spectroscopy," Bunseki Kagaku, 55: 715-720 (2006).

Yokoyama et al., "Determination of Aluminum in Water Samples by Flame AAS after Extraction of 8-quinolinol Complex with Nitrobenzene," Bunseki Kagaku, 55: 757-763 (2006).

Zhu, "Development of Chelating Resin-Packed Minicolumn for Multielement Preconcentration and Determination of Trace Metals in Natural Water," Bunseki Kagaku, 56: 895-896 (2007).

Ministry of the Environment, Japan, "Mercury Analysis Manual," Mar. 2004.

* cited by examiner

METHOD FOR RECOVERING METAL AND KIT FOR RECOVERY OF METAL FOR USE IN THE SAME

CROSS-REFERENCE TO RELATED APPLICATION

This application claims priority from Japanese Patent Application Nos. 2011-083024, 2011-136921, 2011-207907, 2011-207908, and 2012-060102, filed on Apr. 4, 2011, Jun. 21, 2011, Sep. 22, 2011, Sep. 22, 2011, and Mar. 16, 2012, respectively and U.S. Provisional Application Ser. Nos. 61/533,073 and 61/533,121, filed on Sep. 9, 2011 and U.S. Provisional Application Ser. Nos. 61/538,755 and 61/538,766 filed on Sep. 23, 2011, the entire subject matters of which are incorporated herein by reference.

BACKGROUND OF THE INVENTION

The present invention relates to a method for recovering a metal and a kit for recovery of a metal for use in the same. The present invention also relates to a method for analyzing a metal and an analysis apparatus for use in the same.

It is known that metals such as mercury, cadmium, lead, and arsenic accumulate in human bodies, which results in adverse effects on health. Therefore, it is important to analyze metals in biological samples such as urine and the like and samples of food and beverage such as water and the like.

In analyzing a metal, generally, as a pretreatment, foreign substances are removed from a sample, a metal is separated from the resulting sample, and the separated metal is analyzed. In the pretreatment, a solvent extraction is widely used. The solvent extraction is a method in which a metal in a sample is extracted into an organic medium by utilizing the polarity of a chelating agent to be bound to the metal according to the difference in distribution coefficient of the metal to an aqueous medium and the organic medium. The metal can be further concentrated by evaporating the organic medium after the extraction. As a specific example of the solvent extraction, a dithizone method using, as the chelating agent, 1,5-diphenyl-3-thiocarbazone (hereinafter, also referred to as "dithizone") that is insoluble in an aqueous medium under acidic conditions is defined in JIS, for example (see, Mercury Analysis Manual, Ministry of the Environment, March 2004, Japanese Patent No. 2969226). In the dithizone method, first, dithizone and a liquid sample such as urine are mixed under acidic conditions, and a complex between the dithizone and a metal present in the liquid sample is formed in the mixture. Subsequently, an organic medium such as carbon tetrachloride or chloroform is added to the mixture. Then, the complex is extracted into the organic medium because the distribution coefficient of the complex to the aqueous medium is different from that of the complex to the organic medium. Thereafter, this organic medium is recovered. Thus, the metal is recovered as the complex from the liquid sample. When the organic medium is evaporated, the metal can be further concentrated.

However, it is essential to use an organic medium in the conventional solvent extraction method as mentioned above. In the case of using an organic medium, handling thereof is complicated, and there is a risk that a waste liquid thereof affects the environment. Moreover, in order to concentrate the metal extracted using the organic medium, a decompressor for evaporating the organic medium is required, for example.

BRIEF SUMMARY OF THE INVENTION

The present invention is intended to provide a method for recovering a metal without requiring the use of an organic medium.

In order to achieve the aforementioned object, the present invention provides a method for recovering a metal, the method including the steps of: forming a first complex between a first chelating agent and a metal present in a sample in a first mixture prepared by mixing the first chelating agent and the sample; recovering the first complex from the first mixture; forming a second complex between the metal derived from the first complex and a second chelating agent in a second mixture prepared by mixing the first complex and an aqueous solution of the second chelating agent; and recovering the metal by recovering a liquid fraction containing the second complex dissolved therein from the second mixture, wherein in the step of forming a first complex, the first mixture is prepared under pH conditions where the first chelating agent can be insoluble in an aqueous medium, and in the step of forming a second complex, the aqueous solution of the second chelating agent is under pH conditions where the first chelating agent can be insoluble therein.

The present invention also provides a kit for recovery of a metal, for use in the method for recovering a metal of the present invention, the kit including: a first chelating agent; and a second chelating agent.

The present invention also provides an analysis apparatus including: a pH adjusting unit for adjusting a pH; a first mixing unit for mixing a first chelating agent and a sample; a complex recovering unit for recovering a first complex between the first chelating agent and a metal present in the sample from a first mixture containing the first chelating agent and the sample; a second mixing unit for mixing an aqueous solution of a second chelating agent and the first complex; a liquid fraction recovering unit for recovering a liquid fraction containing a second complex between the metal derived from the first complex and the second chelating agent, dissolved therein, from a second mixture of the aqueous solution of the second chelating agent and the first complex; a metal recovering unit for recovering the metal present in the second complex, and an analyzing unit for analyzing the recovered metal, wherein the analysis apparatus is for use in a method for analyzing a metal.

According to the present invention, a metal can be recovered easily by utilizing the difference in solubility between the first chelating agent and the second chelating agent in an aqueous medium without substantially using an organic medium. Therefore, the present invention is useful in clinical examinations of samples derived from biological bodies and environmental testing, for example.

DETAILED DESCRIPTION OF THE INVENTION

Method for Recovering Metal

A method for recovering a metal (hereinafter merely referred to as the "metal recovering method") of the present invention is, as mentioned above, a method for recovering a metal, the method including the steps of: forming a first complex between a first chelating agent and a metal present in a sample in a first mixture prepared by mixing the first chelating agent and the sample; recovering the first complex from the first mixture; forming a second complex between the metal derived from the first complex and a second chelating agent in a second mixture prepared by mixing the first complex and an aqueous solution of the second chelating agent; and recovering the metal by recovering a liquid fraction containing the second complex dissolved therein from the second mixture, wherein in the step of forming a first complex, the first mixture is prepared under pH conditions where the first chelating agent can be insoluble in an aqueous medium, and in the step of forming a second complex, the aqueous solution of the second chelating agent is under pH conditions where the first chelating agent can be insoluble therein.

In the metal recovering method of the present invention, the chelating agent preferably is a chelating agent comprising a sulfur-containing group. The sulfur-containing group is a functional group having a sulfur atom. The sulfur-containing group may be a thioketone group or comprises a thioketone group, for example. The thioketone group is not particularly limited and examples thereof include a thiocarbazone group, a thiosemicarbazone group, a thiocarbadiazone group, a thiourea group, a thiosemicarbazide group, and a rubeamate group.

Thiocarbazone Group

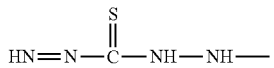

Thiosemicarbazone Group

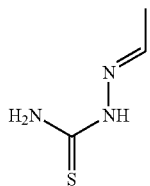

Thiocarbadiazone Group

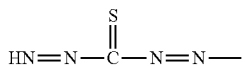

Thiourea Group

Thiosemicarbazide Group

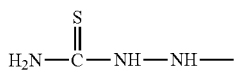

Rubeamate Group

The first chelating agent can be, for example, a chelating agent represented by the structural formula (1) or (2).

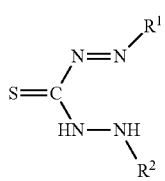

(1)

In the structural formula (1), $R^1$ and $R^2$ each represents a phenyl group. That is, the first chelating agent represented by the structural formula (1) is a chelating agent comprising a thiocarbazone group and can be 1,5-diphenyl-3-thiocarbazone. Hereinafter, the first chelating agent is also referred to as dithizone. The chelating agent represented by the structural formula (1) may be, for example, a salt.

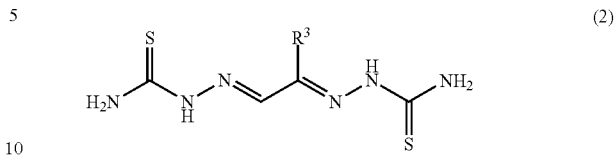

(2)

In the structural formula (2), $R^3$ represents hydrogen, an alkyl group, or a phenyl group. The chelating agent represented by the structural formula (2) may be, for example, a salt.

The alkyl group is not particularly limited, and examples thereof include straight-chain or branched alkyl groups. The carbon number of the alkyl group is, for example, from 1 to 6. Examples of the straight-chain or branched alkyl groups include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a n-heptyl group, a n-octyl group, a n-nonyl group, and a n-decyl group. Any hydrogen in the alkyl group may be substituted, for example.

Any hydrogen in the phenyl group may be substituted, for example. For example, the hydrogen in the phenyl group may be substituted by halogen or an alkali metal such as sodium or potassium when substituted.

In the metal recovering method of the present invention, the chelating agent represented by the structural formula (2) is, for example, a chelating agent comprising a thiosemicarbazone group, and examples thereof include glyoxaldithiosemicarbazone and (1E,2E)-aminocarbothioyl hydrazono phenylethanal thiosemicarbazone.

In the metal recovering method of the present invention, the chelating agent preferably is a chelating agent comprising a sulfur-containing group as mentioned above. The sulfur-containing group can be, for example, a thioketone group. The chelating agent comprising a thioketone group can be, for example, a chelating agent comprising at least one selected from the group consisting of a thiocarbazone group, a thiosemicarbazone group, a thiocarbadiazone group, a thiourea group, a thiosemicarbazide group, and a rubeamate group. As specific examples of the chelating agent, the following chelating agents are illustrated. In the present invention, the following chelating agents are mere examples, and the present invention is not limited thereby.

(a1) Chelating agent comprising a thiocarbazone group
e.g., 1,5-di(2-naphtyl)thiocarbazone;
(a2) Chelating agent comprising a thiosemicarbazone group
e.g., acetone thiosemicarbazone, acetophenone thiosemicarbazone;
(a3) Chelating agent comprising a thiocarbadiazone group
e.g., diphenylthiocarbadiazone;
(a4) Chelating agent comprising a thiourea group
e.g., 1-acetyl-2-thiourea, guanyl thiourea, 1,3-bis(dimethylaminopropyl)-2-thiourea, tetramethyl thiourea, N,N'-diethyl thiourea, N,N'-diisopropyl thiourea, N,N'-dibutyl thiourea, 1,3-bis(dimethylaminopropyl)-2-thiourea, N-allyl-N'-(2-hydroxyethyl)thiourea, N,N'-bis(2-hydroxyethyl)thiourea, diacetyl thiourea, phenyl thiourea, N,N'-diphenyl thiourea, mono-o-tolyl thiourea, N,N'-di-o-tolyl thiourea, benzoyl thiourea;

(a5) Chelating agent comprising a thiosemicarbazide group
e.g., phenylthiosemicarbazide, 4-phenylthiosemicarbazide, 4-methylthiosemicarbazide, thiosemicarbazide;
(a6) Chelating agent comprising a rubeamate group
e.g., dithiooxamide (rubeanic acid).

In the metal recovering method of the present invention, the second chelating agent is, for example, preferably a chelating agent comprising a thiol group.

The second chelating agent is not particularly limited and can be, for example, a chelating agent comprising a structure represented by the structural formula (3), (4), or (5).

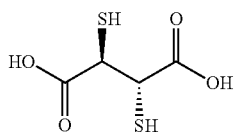
(3)

The second chelating agent comprising a structure represented by the structural formula (3) is meso-2,3-dimercapto succinic acid. Hereinafter, the second chelating agent is also referred to as DMSA.

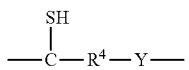
(4)

In the chelating agent comprising a structure represented by the structural formula (4), $R^4$ represents an alkyl group with the carbon number of 1 or 2 or is not present, and Y represents

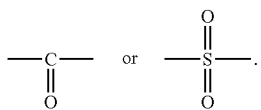

The alkyl group with the carbon number of 1 or 2 is, for example, a methyl group or an ethyl group.

Examples of the second chelating agent comprising a structure represented by the structural formula (4) include thiopronine (N-(2-mercaptopropionyl)glycine) represented by the following structural formula (4-1), DMPS (2,3-dimercapto-1-propanesulfonic acid sodium salt) represented by the following structural formula (4-2), and cysteine (2-amino-3-sulfanyl propanoic acid) represented by the following structural formula (4-3).

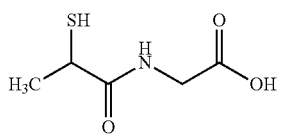
(4-1)

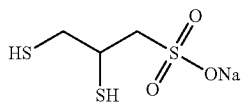
(4-2)

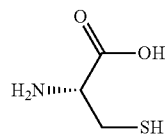
(4-3)

HS—$R^5$—Y— (5)

In the chelating agent comprising a structure represented by the structural formula (5), $R^5$ represents an aromatic hydrocarbon group, and Y represents

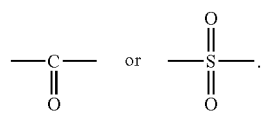

$R^5$ represents an aromatic hydrocarbon group with the carbon number from 1 to 10, for example, and examples thereof include a phenyl group, a benzyl group, a tolyl group, and a naphthyl group.

The second chelating agent comprising a structure represented by the structural formula (5) can be, for example, a chelating agent represented by the following structural formula (5-1). In the structural formula (5-1), $R^6$ represents a hydroxyl group, for example.

HS—$R^5$—Y—$R^6$ (5-1)

The chelating agent represented by the structural formula (5-1) may be a salt, for example, and examples of the salt include alkali metal salts such as a sodium salt and a potassium salt. Specific examples of the chelating agent represented by the structural formula (5-1) include thiosalicylic acid represented by the following structural formula (5-2) and sodium thiosalicylate represented by the following structural formula (5-3).

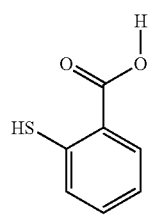
(5-2)

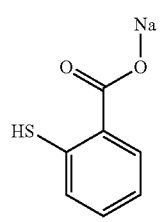
(5-3)

Each of the first chelating agent and the second chelating agent may be, for example, any of tautomers and stereoisomers of the above-mentioned compounds. Examples of the isomers include geometric isomers, conformers, and stereoisomers. Each of the first chelating agent and the second chelating agent may be, for example, any of hydrates of the above-mentioned compounds. Each of the first chelating agent and the second chelating agent may be, for example, any of salts of the above-mentioned compounds, and examples of the salts include alkali metal salts such as a sodium salt and a potassium salt. In the above-mentioned compounds as the first chelating agent and the second chelating agent, any hydrogen may be substituted, for example, and specifically, any hydrogen may be substituted by an alkali metal such as halogen, sodium, or potassium, for example. As the first chelating agent and the second chelating agent, commercially available products may be used. The thiopronine is available from KANTO CHEMICAL CO., INC., Tokyo Chemical Industry Co., Ltd., Wako Pure Chemical Industries, Ltd., or the like, for example. The DMPS is available from Wako Pure Chemical Industries, Ltd. or the like, for example. The cysteine is available from NACALAI TESQUE, INC. or the like, for example.

The first chelating agent may be used alone or in a combination of two or more of them, for example. The second chelating agent may be used alone or in a combination of two or more of them.

The combination of the first chelating agent and the second chelating agent is not particularly limited. Examples of the combination include: combinations of the first chelating agent represented by the structural formula (1) with the second chelating agent comprising a structure represented by the structural formula (3), the second chelating agent comprising a structure represented by the structural formula (4), and the second chelating agent comprising a structure represented by the structural formula (5); and combinations of the first chelating agent represented by the structural formula (2) with the second chelating agent comprising a structure represented by the structural formula (3), the second chelating agent comprising a structure represented by the structural formula (4), and the second chelating agent comprising a structure represented by the structural formula (5). Among them, any of the combinations of the first chelating agent represented by the structural formula (1) with the second chelating agent comprising a structure represented by the structural formula (3), the second chelating agent comprising a structure represented by the structural formula (4), and the second chelating agent comprising a structure represented by the structural formula (5) and the combination of the first chelating agent represented by the structural formula (2) and the second chelating agent comprising a structure represented by the structural formula (4) is preferable. Specific examples of the combination include a combination of dithizone and DMSA, a combination of dithizone and thiopronine or DMPS, a combination of dithizone and sodium thiosalicylate, and a combination of glyoxaldithiosemicarbazone and thiopronine.

In the metal recovering method of the present invention, the metal to be recovered is not particularly limited. Examples thereof include Bi (bismuth), Hg (mercury), Cd (cadmium), Pd (palladium), Zn (zinc), Tl (thallium), Ag (silver), Pb (lead), and As (arsenic). The form of the metal in the sample is not particularly limited and may be, for example, a single metal, an alloy of metals, or a metal-containing compound. The metal-containing compound may be, for example, a metal-containing organic compound or a metal-containing inorganic compound. In the case where the metal is Hg, Hg may be, for example, organic mercury or inorganic mercury. In the metal recovering method of the present invention, the metal to be recovered may be, for example, one kind or two or more kinds. In the metal recovering method of the present invention, two or more kinds of metals can be recovered at the same time by a single recovering treatment, for example.

In the metal recovering method of the present invention, the sample is not particularly limited. Examples thereof include a sample derived from a biological body, a sample derived from the environment, a chemical substance, and a pharmaceutical. Examples of the chemical substance include reagents, pesticides, and cosmetics. The sample derived from a biological body is not particularly limited, and examples thereof include urine, blood, hair, and umbilical cords. Examples of the blood sample include erythrocytes, whole blood, sera, and plasma. Among them, the urine sample is preferable. The sample derived from the environment is not particularly limited, and examples thereof include an organism, food, water, the ground, and atmosphere and air. Examples of the organism include animals such as the human and fish and shellfish and plants. Examples of the food sample include a fresh food and a processed food. Examples of the water sample include drinking water, groundwater, river water, seawater, and domestic sewage.

A fluid sample (liquid sample) is preferable as the sample because it can be handled easily, for example. An undiluted liquid or a diluted liquid obtained by suspending, dispersing, or dissolving the sample in a medium may be used as the liquid sample, for example. In the case where the sample is a solid, a diluted liquid obtained by suspending, dispersing, or dissolving the solid in a medium may be used as the liquid sample, for example. Hereinafter, the medium is referred to as a dilution medium. The dilution medium is not particularly limited, and examples thereof include water and a buffer solution. The buffer solution is not particularly limited and examples thereof include a tris(hydroxymethyl)aminomethane buffer solution (tris buffer solution), a phosphate buffer solution, an acetate buffer solution, a borate buffer solution, a citrate buffer solution, a veronal buffer solution, and various Good buffer solutions. The concentration of the buffer solution is not particularly limited and is, for example, from about 10 to about 100 mmol/L.

According to the present invention, it is not necessary to use an organic medium as mentioned above, and the recovery rate and concentration rate of a metal can be improved compared with those obtained by the conventional method using an organic medium, for example.

(1) Step of Forming First Complex

A step of forming a first complex is a step of forming a first complex between a first chelating agent and a metal present in a sample in a first mixture prepared by mixing the first chelating agent and the sample. In the step of forming a first complex, the first mixture is prepared under pH conditions where the first chelating agent can be insoluble in an aqueous medium. Hereinafter, the "pH conditions where the first chelating agent can be insoluble in an aqueous medium" is also referred to as the "first pH conditions".

The first chelating agent can maintain the state of being undissolved in the first mixture under the first pH conditions. Therefore, when a metal is present in the sample, a first complex between the first chelating agent and the metal present in the sample is formed in the first mixture. The first chelating agent is, for example, preferably in the state of not being completely dissolved in the first mixture and, however, may be in the state of being partially dissolved in the first mixture. In the latter case, for example, even in the case where the first chelating agent is partially dissolved in the first mixture, it is only necessary that the amount of the remaining first chelating agent being present in the first mixture in the state of being undissolved therein is the amount capable of forming a first complex with the metal.

The first pH conditions can be set as appropriate according to the kinds of the first chelating agent to be used and the metal to be recovered. In the step of forming a first complex, the pH conditions for insolubilization are not particularly limited. The first pH conditions can be, for example, acidic conditions (about pH 5 or less), neutral conditions (about pH 6 to about pH 7), and alkaline conditions (more than about pH 7 to about pH 8 or less). In an exemplary embodiment, the upper limit thereof is, for example, about pH 8, and the lower limit thereof is, for example, about pH 1. Specific examples thereof include pH 1 to 8, with all values in-between, such as pH 2 to 8, such as pH 1 to 2.

It is only necessary that the first mixture containing the first chelating agent and the sample is substantially an aqueous medium. The aqueous medium is a non-organic medium, means a so-called aqueous liquid, and can also be referred to as an aqueous solvent. "Substantially an aqueous medium" means that it may be an aqueous medium containing the trace amount of an organic medium (so-called organic solvent) as compared to the pure aqueous medium, for example.

The form of the first chelating agent at the time of mixing with the sample is not particularly limited, and the first chelating agent may be in a dry state (or also referred to as the solid state) or in the liquid state, for example. In the latter case, the first chelating agent is preferably a first chelating agent-dispersion liquid obtained by dispersing the first chelating agent in a non-organic medium in which the first chelating agent cannot be dissolved. Hereinafter, the non-organic medium in which the first chelating agent is dispersed is referred to as a "dispersion medium". The dispersion medium is, for example, a non-organic medium (aqueous medium) under the first pH conditions. In the case where the first pH conditions are acidic conditions, examples of the dispersion medium include an acid, an acid aqueous solution, and a buffer solution under acidic conditions. In the case where the first pH conditions are alkaline conditions, examples of the dispersion medium include an alkali, an alkali aqueous solution, and a buffer solution under alkaline conditions. In the case where the first pH conditions are neutral conditions, examples of the dispersion medium include the acid, the acid aqueous solution, the buffer solution under acidic conditions, the alkali, the alkali aqueous solution, and the buffer solution under alkaline conditions in addition to water, a neutral aqueous solution, and a buffer solution under neutral conditions.

The acid is not particularly limited, and examples thereof include hydrochloric acid, sulfuric acid, acetic acid, boric acid, phosphoric acid, and citric acid. The acid aqueous solution can be, for example, one obtained by diluting an acid with water or a buffer solution. The buffer solution for use in the dilution of the acid is not particularly limited, and any of the above-mentioned general buffer solutions can be used. The concentration of the acid in the acid aqueous solution is not particularly limited and is, for example, more than about 0N to about 1N or less, preferably from about 0.01N to about 0.1N. The buffer solution under acidic conditions is not particularly limited, and examples thereof include a citrate buffer solution, an acetate buffer solution, a phosphate buffer solution, and Good buffer solutions. The concentration of the buffer solution under acidic conditions is not particularly limited and is, for example, from about 10 to about 100 mmol/L.

The neutral aqueous solution is not particularly limited, and examples thereof include a physiological saline solution, a phosphate buffer solution, and a tris buffer solution. The buffer solution under neutral conditions is not particularly limited. The concentration of the buffer solution under neutral conditions is not particularly limited and is, for example, from about 10 to about 100 mmol/L.

The alkali is not particularly limited, and examples thereof include sodium hydroxide and potassium hydroxide. The alkali aqueous solution can be, for example, one obtained by diluting an alkali with water or a buffer solution. The buffer solution for use in the dilution of the alkali is not particularly limited, and any of the above-mentioned general buffer solutions can be used. The concentration of the alkali in the alkali aqueous solution is not particularly limited and is, for example, more than about 0N to about $7 \times 10^{-3}$N or less. The buffer solution under alkaline conditions is not particularly limited, and examples thereof include Tris-NaOH, Tris-HCl, a phosphate buffer solution, a sodium phosphate buffer solution, a carbonate buffer solution, and Good buffer solutions. The concentration of the buffer solution under alkaline conditions is not particularly limited and is, for example, from about 10 to about 100 mmol/L.

A method for mixing the sample and the first chelating agent is not particularly limited. The method may be, for example, (1a) mixing the sample where the pH conditions have been previously adjusted to the first pH conditions and the first chelating agent, (1b) mixing the first chelating agent where the pH conditions have been previously adjusted to the first pH conditions and the sample, or (1c) mixing a non-organic medium under the first pH conditions, the first chelating agent, and the sample.

In the method (1a), for example, the mixture under the first pH conditions can be prepared by mixing the sample where the pH conditions have been adjusted to the first pH conditions and the first chelating agent, and thus the first complex can be formed in the first mixture. At that time, for example, the pH of the sample is adjusted so that the first mixture prepared by mixing the first chelating agent and the sample is under the first pH conditions.

In the case where the first pH conditions are acidic conditions, a method for adjusting the pH conditions of the sample to acidic conditions is not particularly limited, for example. The adjustment can be performed by adding an acidic regent to the sample, for example. Examples of the acidic reagent include an acid, an acid aqueous solution, and a buffer solution under acidic conditions. The acid is not particularly limited, and examples thereof include hydrochloric acid, sulfuric acid, citric acid, boric acid, phosphoric acid, and acetic acid. The acid aqueous solution can be, for example, one obtained by diluting an acid with water or a buffer solution. The buffer solution for use in the dilution of the acid is not particularly limited, and any of the above-mentioned general buffer solutions can be used. The concentration of the acid in the acid aqueous solution is not particularly limited and is, for example, from about 0.01N to about 5N. The buffer solution under acidic conditions is not particularly limited, and examples thereof include a citrate buffer solution, an acetate buffer solution, a phosphate buffer solution, and Good buffer solutions. The concentration of the buffer solution under acidic conditions is not particularly limited and is, for example, from about 10 to about 100 mmol/L.

In the case where the first pH conditions are alkaline conditions, a method for adjusting the pH conditions of the sample to alkaline conditions is not particularly limited, for example. The adjustment can be performed by adding an alkaline reagent to the sample, for example. Examples of the alkaline regent include an alkali, an alkali aqueous solution, and a buffer solution under alkaline conditions such as mentioned above.

In the case where the first pH conditions are neutral conditions, a method for adjudging the pH conditions of the sample to neutral conditions is not particularly limited, for example. The adjustment can be performed by adding the acidic reagent, the alkaline reagent, or a neutral reagent to the sample according to the original pH conditions of the sample, for example. Examples of the neutral reagent include water, a neutral aqueous solution, and a buffer solution under neutral conditions such as mentioned above.

In the method (1b), for example, the first mixture under the first pH conditions can be prepared by mixing the sample and the first chelating agent where the pH conditions have been adjusted to the first pH conditions, and thus the first complex can be formed in the first mixture. At that time, for example, the pH of the first chelating agent is adjusted so that the first mixture prepared by mixing the sample and the first chelating agent is under the first pH conditions.

A method for adjusting the pH conditions of the first chelating agent to the first pH conditions is not particularly limited. Specifically, by dispersing the first chelating agent in a dry state in a non-organic medium in which the first chelating agent cannot be dissolved, the first chelating agent-dispersion liquid where the pH conditions have been adjusted to the first pH conditions can be obtained. As the non-organic medium in which the first chelating agent is dispersed, any of the above-mentioned dispersion media such as the acidic reagent, the alkaline regent, and the neutral reagent can be used, for example.

The first chelating agent in a dry state is superior in dispersibility in a non-organic medium, for example. Therefore, a dried chelating agent obtained by freeze-drying or drying under reduced pressure is preferable. A method for producing the dried first chelating agent is not particularly limited, and for example, the dried first chelating agent is obtained by mixing a first chelating agent into an organic medium, and thereafter freeze-drying the mixture or drying the mixture under reduced pressure. The organic medium is not particularly limited, and for example, t-butyl alcohol or 2-propanol can be used.

In the method (1c), for example, the first mixture under the first pH conditions can be prepared by mixing the non-organic medium under the first pH conditions, the first chelating agent, and the sample, and thus the first complex can be formed in the first mixture. At that time, for example, the pH of the non-organic medium is adjusted so that the first mixture prepared by mixing the first chelating agent, the sample, and the non-organic medium is under the first pH conditions. As the non-organic medium under the first pH conditions, the acidic reagent, the alkaline reagent, the neutral reagent, or the like such as mentioned above can be used, for example.

A method for mixing the first chelating agent and the sample is not particularly limited, and examples thereof include conventional methods such as mixing by repeatedly turning upside down, mixing by vibrating, and mixing by ultrasound.

The concentration of the first chelating agent in the first mixture is not particularly limited and is, for example, in the range from 0.1 to 2 mg. Specifically, the concentration of the first chelating agent represented by the structural formula (1) in the first mixture is, for example, in the range from 0.1 to 1.5 mg/mL, preferably from 0.1 to 0.3 mg/mL. The concentration of the first chelating agent represented by the structural formula (2) in the first mixture is, for example, in the range from 0.3 to 2 mg/mL, preferably from 1 to 2 mg/mL.

The concentration of the sample in the first mixture is not particularly limited and is, for example, in the range from 0.1 to 100 µg/L. The concentration of an undiluted sample in the first mixture is preferably in the above-described range.

The ratio between the first chelating agent and the sample in the first mixture is not particularly limited and is, for example, in the range from 0.1 to 2 mg of the first chelating agent per 1 mL of the sample. Specifically, with respect to the first chelating agent represented by the structural formula (1), the ratio is, for example, in the range from 0.1 to 1.5 mg of the first chelating agent, preferably from 0.1 to 0.3 mg of the first chelating agent, per 1 mL of the sample, and with respect to the first chelating agent represented by the structural formula (2), the ratio is, for example, in the range from 0.3 to 2 mg of the first chelating agent, preferably from 1 to 2 mg of the first chelating agent, per 1 mL of the sample.

The first mixture may contain other component besides the first chelating agent and the sample. The other component is not particularly limited, and examples thereof include an oxidizing agent and a reducing agent. The oxidizing agent can be used for improving reactivity of a reaction for forming a first complex between the first chelating agent and the metal, for example. The reducing agent can be used for canceling the excess amount of the oxidizing agent when the first mixture contains the excess amount of the oxidizing agent, for example.

The treatment conditions for forming the first complex are not particularly limited, and the treatment temperature is, for example, room temperature, and the treatment time is, for example, from 10 seconds to 120 minutes. Specifically, the treatment time is, for example, preferably in the range from 10 seconds to 10 minutes, particularly preferably from 10 seconds to 5 minutes.

(2) Step of Recovering First Complex

In the step of recovering a first complex, the first complex formed in the step of forming a first complex is recovered from the first mixture.

As mentioned above, the first chelating agent can maintain the state of being undissolved in the first mixture under the first pH conditions. Therefore, the first complex between the first chelating agent and the metal is also present in the first mixture in the state of being undissolved therein. Thus, in this step of recovering a first complex, the undissolved first complex being present in the first mixture is recovered.

A method for recovering the first complex is not particularly limited, and a conventionally known method for separating a solid from a liquid can be employed, for example. Examples of the method include a centrifugal treatment, a filtration treatment, a precipitation treatment, a membrane separation treatment, an adsorption treatment, and a freeze-drying treatment. The treatment conditions for recovering the first complex are not particularly limited and can be set as appropriate according to the kind or amount of the first complex, for example. In the case where the first complex is recovered by the centrifugal treatment, the treatment conditions can be, for example, the centrifugal acceleration in the range from 19,600 to 29,400 m/s$^2$ (2,000 to 3,000×g), the temperature in the range from 4° C. to room temperature, and the time in the range from 1 to 10 minutes. The first complex can be recovered by removing a supernatant after the centrifugation, for example. In the case where the first complex is recovered by the filtration treatment, a filter to be used is not particularly limited, for example, and examples thereof include a filter paper, filter powder, and a membrane filter. After the filtration treatment, a fraction that has not passed through the filter can be recovered as the first complex.

(3) Step of Forming Second Complex

A step of forming a second complex is a step of forming a second complex between the metal derived from the first complex and a second chelating agent in a second mixture prepared by mixing the first complex and an aqueous solution of the second chelating agent. In the step of forming a second complex, the aqueous solution of the second chelating agent (hereinafter also referred to as the "second chelating agent aqueous solution) is under the pH conditions where the first chelating agent can be insoluble therein. Hereinafter, the "pH conditions where the first chelating agent can be insoluble in the second chelating agent aqueous solution" is also referred to as the "second pH conditions".

The second chelating agent is in the state of being dissolved in the second mixture, and the first complex can maintain the state of being undissolved in the same. Then, when the first complex and the second chelating agent are present in the second mixture, the metal forming the first complex is completely or partially dissociated from the first complex and binds to the second chelating agent, so that a second complex between the second chelating agent and the metal is formed, although the mechanism is unknown.

The second pH conditions are, for example, pH conditions where the second chelating agent can be soluble in an aqueous medium, and the first complex can be insoluble in the same. In the step of forming a second complex, the pH conditions of the second chelating agent aqueous solution and the pH conditions of the second mixture of the aqueous solution and the first complex are both preferably the second pH conditions.

The second pH conditions can be set as appropriate according to the kinds of the first chelating agent, the second chelating agent, and the metal to be recovered, for example. The second pH conditions can be, for example, non-alkaline conditions, and specific examples thereof include acidic conditions (about pH 1 to about pH 3), mildly acidic conditions (about pH 4 to about pH 5), and neutral conditions (about pH 6 to about pH 7). The second pH conditions are not particularly limited, the upper limit thereof is, for example, about pH 6.8, and the lower limit thereof is, for example, about pH 1. Specific Examples of the Second pH Conditions Include pH 1 to 6.8 with all pH Values in-Between.

In the case where the second chelating agent comprises a structure represented by the structural formula (3) or (5), the upper limit of the second pH conditions is, for example, about pH 6.8, preferably about pH 6, and the lower limit of the same is, for example, about pH 1, preferably about pH 2, more preferably about pH 3, yet more preferably about pH 4. Examples of the second pH conditions include from about pH 2 to about pH 6.8, from about pH 2 to about 6, and from about pH 4 to about pH 6.

In the case where the second chelating agent comprises a structure represented by the structural formula (4), the upper limit of the second pH conditions are, for example, about pH 6.8, preferably about pH 6, more preferably about pH 4 and the lower limit of the same therefore is, for example, about pH 1. Examples of the second pH conditions include about pH 1 to about pH 6.8, about pH 1 to about pH 6, about pH 1 to about pH 3, and about pH 1.

It is only necessary that the second chelating agent aqueous solution is obtained by dissolving the second chelating agent in an aqueous medium, for example. The second chelating agent is, for example, preferably in the state of being completely dissolved in the aqueous solution and, however, may be in the state of being partially dissolved in the aqueous solution. In the latter case, for example, it is only necessary that the amount of the remaining second chelating agent being present in the aqueous solution is the amount capable of forming a second complex with the metal derived from the first complex, for example.

The second chelating agent aqueous solution can be prepared by adjusting the pH conditions of an aqueous medium to the second pH conditions and thereafter dissolving a second chelating agent in the aqueous medium, for example.

In the case where the second chelating agent comprises a structure represented by the structural formula (3) or (5), the second chelating agent aqueous solution can be prepared as follows, for example. A second chelating agent is added to the neutral or acidic aqueous solvent. Then, an alkaline reagent is added to this mixture thus obtained so as to adjust the pH conditions of the mixture to the second pH conditions, so that the second chelating agent is dissolved. Thus, the second chelating agent aqueous solution can be prepared. Since the chelating agent comprising a structure represented by the structural formula (3) is a strong acid, it is preferred that the aqueous medium in which the second chelating agent is dissolved is, for example, the alkaline reagent. By dissolving the second chelating agent in the alkaline reagent, the aqueous solution under the second pH conditions, preferably under non-alkaline conditions, can be prepared. The pH of the alkaline reagent is not particularly limited, the lower limit thereof is, for example, about pH 8, preferably about pH 9, more preferably about pH 10, and the upper limit thereof is, for example, about pH 12, preferably about pH 11. The alkaline reagent is not particularly limited and is, for example, preferably an alkaline aqueous solution, more preferably an alkaline buffer solution. The alkaline aqueous solution can be, for example, a trisodium phosphate aqueous solution. Examples of the alkaline buffer solution include a phosphate buffer solution, a tris buffer solution, and Good buffer solutions. The concentrations of the alkaline aqueous solution and the alkaline buffer solution are not particularly limited and are, for example, from about 10 to about 100 mmol/L, preferably about 100 mmol/L.

In the case where the second chelating agent comprises a structure represented by the structural formula (4), the second chelating agent aqueous solution can be prepared as follows, for example. The aqueous medium in which the second chelating agent is dissolved is not particularly limited, and for example, water, an aqueous solution, a buffer solution, or the like can be used. For example, the pH conditions of the aqueous medium are adjusted to the second pH conditions, and thereafter the second chelating agent is dissolved therein. A method for adjusting the pH conditions of the aqueous medium is not particularly limited, and in the method, the acidic reagent, the alkaline reagent, and the neutral reagent can be used as appropriate, for example.

Besides the above-mentioned methods, a method of preparing the second chelating agent aqueous solution can be, for example, a method in which a second chelating agent is added to an aqueous medium, then the pH of the mixture thus obtained is adjusted to the second pH conditions, so that the second chelating agent is dissolved therein.

In this case, the aqueous medium is not particularly limited, and for example, water, an aqueous solution, a buffer solution, or the like can be used. For example, the aqueous medium and the second chelating agent are mixed, and thereafter, the pH conditions of the mixture thus obtained are adjusted to the second pH conditions. A method for adjusting the pH conditions of the mixture is not particularly limited, and in the method, the acidic reagent, the alkaline reagent, and the neutral reagent can be used as appropriate, for example.

The concentration of the second chelating agent in the second chelating agent aqueous solution is not particularly limited and is, for example, from 5 to 300 mg/mL.

In the case where the second chelating agent comprises a structure represented by the structural formula (3) or (5), the concentration of the second chelating agent in the second chelating agent aqueous solution is, for example, from 5 to 20 mg/mL, preferably from 10 to 20 mg/mL.

In the case where the second chelating agent comprises a structure represented by the structural formula (4), the concentration of the second chelating agent in the second chelating agent aqueous solution is, for example, from 15 to 300 mg/mL, preferably from 75 to 150 mg/mL. Among the second chelating agents, thiopronine, DMPS, or cysteine is preferable because of having superior solubility. For example, as the concentration of the second chelating agent in the second chelating agent aqueous solution is increased, the amount of the formed second complex between the metal derived from the first complex and the second chelating agent is increased. Thus, the recovery rate of the metal can be further improved.

A method for mixing the first complex and the second chelating agent aqueous solution is not particularly limited, and examples thereof include conventional methods such as mixing by repeatedly turning upside down, mixing by vibrating, and mixing by ultrasound.

The amount of the second chelating agent aqueous solution to be added in the second mixture is not particularly limited. The amount is, for example, preferably from 10 to 200 µL, more preferably from 20 to 100 µL, yet more preferably 20 µL, per 1 mL of the sample used in the step of forming a first complex. The ratio between the first complex and the second chelating agent to be added in the second mixture is not particularly limited. The ratio (ratio by weight) between the first chelating agent used in the step of forming a first complex and the second chelating agent used in the step of forming a second complex is, for example, from 1:0.3 to 1:40, preferably from 1:7 to 1:40, more preferably from 1:10 to 1:40.

The amount of the second chelating agent aqueous solution to be added to the first complex is not particularly limited. It is preferred that the amount is, for example, less than the fluid amount of the used sample. With this amount, a metal-containing liquid with a metal concentration higher than that of the used sample can be obtained. That is, a metal-containing liquid in which a metal is concentrated as compared with in the sample can be obtained. The amount of the second chelating agent aqueous solution to be added is, for example, in the range from 1/2 to 1/100, preferably from 1/10 to 1/100, more preferably from 1/50 to 1/100, with respect to the fluid amount of the sample.

The second mixture may further contain other component besides the first complex and the second chelating agent aqueous solution. The other component is not particularly limited, and examples thereof include the oxidizing agent and the reducing agent such as mentioned above.

The treatment conditions for forming a second complex are not particularly limited, and the treatment temperature is, for example, room temperature, and the treatment time is, for example, from 10 seconds to 120 minutes. Specifically, the treatment temperature is, for example, preferably in the range from 10 seconds to 10 minutes, particularly preferably from 10 seconds to 5 minutes.

(4) Step of Recovering Metal

In the step of recovering the metal, the metal is recovered by recovering a liquid fraction containing the second complex formed in the step of forming a second complex, dissolved therein, from the second mixture.

As mentioned above, the second chelating agent is in the state of being dissolved in the second mixture under the second pH conditions. Therefore, the second complex between the second chelating agent and the metal is also present in the state of being dissolved in the second mixture. On the other hand, the first chelating agent is in the state where it can be insoluble in the second mixture. Therefore the first chelating agent is present in the state of being undissolved in the second mixture. Thus, the metal is recovered by recovering a liquid fraction containing the second complex dissolved therein in this step of recovering the metal. The second complex is, for example, preferably in the state of not being completely dissolved in the second mixture, and however, may be in the state of being partially dissolved in the second mixture. It is preferred that the amount of the undissolved second complex is the detection limit or less, for example. In the case where the second chelating agent comprises a structure represented by the structural formula (4) or (5), the pH of the second mixture may be any pH in the step of recovering the metal unless the first chelating agent is undissolved in the second mixture, for example.

A method for recovering the liquid fraction is not particularly limited, and a conventionally known method for separating a solid from a liquid can be employed, for example. Examples of the method include a centrifugal treatment, a filtration treatment, a precipitation treatment, a membrane separation treatment, and an adsorption treatment. The treatment conditions for recovering the liquid fraction are not particularly limited and can be set as appropriate according to the kind or amount of the second complex, for example. In the case where the liquid fraction (second complex) is recovered by the centrifugal treatment, the treatment conditions can be, for example, the centrifugal acceleration in the range from 19,600 to 29,400 m/s$^2$ (2,000 to 3,000×g), the temperature in the range from 4° C. to room temperature, and the time in the range from 1 to 10 minutes. The liquid fraction can be recovered by recovering a supernatant after the centrifugation, for example. In the case where the liquid fraction is recovered by the filtration treatment, a filter to be used is not particularly limited, for example, and examples thereof include a filter paper, filter powder, and a membrane filter. After the filtration treatment, a fraction passed through the filter can be recovered as the liquid fraction.

In the metal recovering method of the present invention, the step of recovering the metal may further include the step of decomposing the second chelating agent in the second complex after recovering the liquid fraction. By decomposing the second chelating agent, a single metal can be recovered from the second complex. A metal can be analyzed stably with superior sensitivity by using the sample obtained by the metal recovering method of the present invention regardless of the kinds of the method for decomposing the second chelating agent and the method for analyzing the metal and the metal concentration in the sample to be applied to the analysis, although the mechanism is unknown, for example.

A method for decomposing the second chelating agent is not particularly limited and can be, for example, a conventionally known method such as ashing. Examples of the ashing include wet ashing and dry ashing. The wet ashing can be performed according to the Mercury Analysis Manual (Ministry of the Environment, March 2004), for example.

The metal recovering method of the present invention is described below with reference to, as an example, a method for recovering mercury as a metal, using acidic conditions as the first pH conditions, mildly acidic conditions to neutral conditions as the second pH conditions, and an urine sample as the sample. This, however, is a mere example, and the present invention is not limited thereby.

First, the pH of an urine sample is adjusted to acidic conditions by adding an acidic reagent thereto.

The amount of the urine sample is not particularly limited and is, for example, in the range from 1 to 100 mL, preferably from 1 to 20 mL, more preferably from 5 to 10 mL. The pH of the urine sample is adjusted to, for example, preferably from about 1 to about 4, more preferably from about 1 to about 2. The amount of the acidic reagent to be added is not particularly limited and is, for example, in the range from 1 to 10 µL per 1 mL of the urine sample. The acidic reagent is, for example, preferably an hydrochloric acid aqueous solution, and the normality thereof is, for example, in the range from about 1N to about 8N.

A dried first chelating agent obtained by freeze-drying is placed in a tube, and further, the urine sample where the pH has been adjusted is added thereto. Thus, a first mixture is prepared. The amount of the first chelating agent is, for example, from 0.1 to 2 mg per 1 mL of the urine sample. At that time, the pH of the first mixture is, for example, from about pH 1 to about pH 4, preferably from about pH 1 to about pH 2. In the case where the first chelating agent is represented by the structural formula (1), preferably dithizone, the amount of the first chelating agent is, for example, from 0.1 to 1.5 mg, preferably from 0.1 to 0.3 mg, more preferably 0.3 mg, per 1 mL of the urine sample. At that time, the pH of the first mixture is, for example, from about 1 to about 4, preferably from about 1 to about 2. In the case where the first chelating agent is represented by the structural formula (2), preferably glyoxaldithiosemicarbazone, the amount of the first chelating agent is, for example, in the range from 0.3 to 2 mg, preferably from 1 to 2 mg, per 1 mL of the urine sample. At that time, the pH of the first mixture is, for example, from about 1 to about 4, preferably from about 1 to about 2.

The prepared first mixture is stood for the predetermined time, so that a first complex between the first chelating agent and mercury being in the urine sample is formed. The treatment temperature is, for example, room temperature, and the treatment time is, for example, from 10 seconds to 120 minutes. Specifically, the treatment time is, for example, preferably in the range from 10 seconds to 10 minutes, particularly preferably from 10 seconds to 5 minutes.

Then, the first mixture is subjected to centrifugation, so that a precipitate containing the first complex is separated from a supernatant. Thereafter, the supernatant is removed, and a second chelating agent aqueous solution is added to the first complex being in the tube, so that the second complex is formed in a second mixture of the first complex and the second chelating agent aqueous solution. The second chelating agent aqueous solution is the same as mentioned above, for example.

In the case where the second chelating agent is a chelating agent comprising a structure represented by the structural formula (3) or (5), such as, for example, DMSA or sodium thiosalicylate, the second chelating agent aqueous solution can be prepared by dissolving the second chelating agent in an alkaline aqueous solution, for example. The alkaline aqueous solution is, for example, preferably a trisodium phosphate aqueous solution. The concentration thereof is, for example, from 10 to 100 mmol/L, and the pH thereof is, for example, from about 9 to about 12. The concentration of the second chelating agent in the second chelating agent aqueous solution is, for example, from 5 to 20 mg/mL, and the pH of the second chelating agent aqueous solution is, for example, from about 2 to about 6, preferably from about 4 to about 6. The pH of the second mixture of the first complex and the second chelating agent aqueous solution is, for example, from about 2 to about 6, preferably from about 4 to about 6.

In the case where the second chelating agent comprises a structure represented by the structural formula (4), such as, for example, DMPS, thiopronine, the second chelating agent aqueous solution can be prepared by dissolving the second chelating agent in a solvent, for example. Examples of the solvent include a trisodium phosphate aqueous solution, nitric acid, acetic acid, phosphoric acid, citric acid, a phosphate buffer solution, and a tris buffer solution, and the concentration thereof is, for example, from about 10 to about 100 mmol/L. The pH of the solvent is not particularly limited as long as it is in the range in which the first chelating agent cannot be dissolved therein. The concentration of the second chelating agent in the second chelating agent aqueous solution is, for example, from 15 to 300 mg/mL, and the pH of the second chelating agent aqueous solution is, for example, from about 1 to about 6, preferably from about 1 to about 3, more preferably about 1. The pH of the second mixture of the first complex and the second chelating agent aqueous solution is, for example, from about 1 to about 6, preferably from about 1 to about 3, and more preferably about 1.

Then, the second mixture is subjected to centrifugation, so that a precipitate containing the second complex is separated from a supernatant. Thereafter, the supernatant is recovered.

As described above, mercury in the state of being the second complex, being dissolved in the liquid fraction, can be recovered. Only mercury can be recovered by decomposing the second chelating agent in the second complex by wet ashing, for example. An example of recovering mercury is explained above, and the present invention, however, is by no means limited thereto. In the metal recovering method of the present invention, two or more kinds of metals can be recovered at the same time by a single recovering treatment, for example. According to the metal recovering method of the present invention, for example, mercury and one or more kinds of the other metals can be recovered at the same time, or two or more kinds of metals other than mercury can be recovered at the same time.

In the present example, dithizone or glyoxaldithiosemicarbazone is shown as the first chelating agent. However, a metal can be recovered in the same manner as mentioned above even in the case of using any of the other first chelating agents. Moreover, DMSA, DMPS, sodium thiosalicylate, or thiopronine is shown as the second chelating agent. However, a metal can be recovered in the same manner as mentioned above even in the case of using any of the other second chelating agents.

<Method for Analyzing Metal>

The method for analyzing a metal (hereinafter merely referred to as the "metal analyzing method") of the present invention is, as mentioned above, a method for analyzing a metal, the method including the steps of recovering a metal from a sample by the metal recovering method of the present invention; and analyzing the metal. The step of recovering a metal can be explained with reference to the explanation of the metal recovering method of the present invention.

The step of analyzing the metal is not particularly limited and can be selected as appropriate according to the kind of the metal to be analyzed, for example. The analysis of the metal can be performed by, for example, an optical measurement, GC-ECD (gas chromatography-electron capture detector), an electrochemical measurement (e.g., stripping voltammetry), a mass spectrometer, or the like. The analysis by the optical measurement can be performed by measuring an absorbance, a transmittance, a reflectance, or the like using an optical analyzer, for example. Examples of the optical analyzer include an atomic absorption spectrometer, a visible spectrometer, and ICP-AES (Inductively Coupled Plasma Atomic Emission Spectrometer). The analysis of the metal may be qualitative analysis or quantitative analysis, for example.

The metal analyzing method of the present invention may further include the step of correcting a measurement value, for example. In the step of correcting a measurement value, a measurement value as a measurement result can be corrected according to the correlation between the measurement value and the metal concentration in a sample, for example. The correlation can be obtained as follows, for example. A metal in the standard samples with the known metal concentrations is recovered by the metal recovering method of the present invention, and measurement values of the metal and the corresponding metal concentrations are plotted. It is preferred that the standard samples are in a dilution series. By correcting measurement values as described above, it becomes possible to perform the quantitative determination with higher reliability.

The metal as the above-mentioned second complex may be analyzed, or the metal as a single metal obtained by isolating the metal from the second complex may be analyzed, for example. In the former case, the step of decomposing the second chelating agent can be omitted, and therefore, the metal can be analyzed more easily at low cost, for example. In the latter case, it is preferred that the step of recovering the metal includes the step of decomposing the second chelating agent being in the second complex, i.e., the step of isolating the metal from the second complex.

<Kit for Recovery of Metal>

The kit for recovery of a metal of the present invention is a kit for recovery of a metal, for use in the metal recovering method of the present invention, the kit including: a first chelating agent; and a second chelating agent. The first chelating agent and the second chelating agent can be explained with reference to the explanation of the metal recovering method of the present invention, for example. It is preferred that the first chelating agent and the second chelating agent are stored in different containers.

The kit may further include a pH adjusting reagent, for example. The pH adjusting reagent is not particularly limited and is, for example, an acidic reagent, a neutral reagent, and an alkaline reagent. The acidic reagent, the neutral reagent, and the alkaline reagent can be explained with reference to the explanation of the metal recovering method of the present invention, for example. It is preferred that the first chelating agent, the second chelating agent, and the pH adjusting reagent are stored in different containers.

The kit may further include other reagent besides the first chelating agent, the second chelating agent, and the pH adjusting reagent, for example. The other reagent is not particularly limited, and examples thereof include the oxidizing agent and the reducing agent such as mentioned above.

<Analysis Apparatus>

The analysis apparatus of the present invention is, as mentioned above, an analysis apparatus including: a pH adjusting unit for adjusting a pH; a first mixing unit for mixing a first chelating agent and a sample; a complex recovering unit for recovering a first complex between the first chelating agent and a metal present in the sample from a first mixture containing the first chelating agent and the sample; a second mixing unit for mixing an aqueous solution of a second chelating agent and the first complex; a liquid fraction recovering unit for recovering a liquid fraction containing a second complex between the metal derived from the first complex and the second chelating agent, dissolved therein, from a second mixture of the aqueous solution of the second chelating agent and the first complex; a metal recovering unit for recovering the metal present in the second complex, and an analyzing unit for analyzing the recovered metal, wherein the analysis apparatus is for use in a method for analyzing a metal. Specifically, it is preferred that the analysis apparatus of the present invention is for use in the method for analyzing a metal of the present invention. The pH adjusting unit includes an acid adding unit and an alkali adding unit, for example. In the analysis apparatus of the present invention, the mixing unit for mixing the first chelating agent and the sample is referred to as a first mixing unit, for example, the mixing unit for mixing a second chelating agent aqueous solution and the first complex is referred to as a second mixing unit, for example.

The acid adding unit includes: a suction-and-discharge unit for sucking and discharging an acidic reagent arranged inside or outside the analysis apparatus; and a controlling unit for controlling the amount of the acidic reagent to be sucked and/or discharged, for example. The suction-and-discharge unit can be, for example, a pump. The controlling unit can be, for example, a valve.

The alkali adding unit includes: a suction-and-discharge unit for sucking and discharging an alkaline reagent arranged inside or outside the analysis apparatus; and a controlling unit for controlling the amount the alkaline reagent to be sucked and/or discharged, for example. The suction-and-discharge unit and the controlling unit can be, for example, the same as mentioned above. The alkali adding unit may also serve as the acid adding unit.

Examples of the first mixing unit include a stirrer, a suction-and-discharge unit, a shaker, and an ultrasound generator.

Examples of the complex recovering unit include a centrifuge, a filtration unit, and a freeze-dryer.

The second adding unit includes: a suction-and-discharge unit for sucking and discharging the second chelating agent aqueous solution arranged inside or outside the analysis apparatus; and a controlling unit for controlling the amount of the second chelating agent aqueous solution to be sucked and/or discharged, for example. The suction-and-discharge unit and the controlling unit can be, for example, the same as mentioned above.

Examples of the liquid fraction recovering unit include a centrifuge, a filtration unit, and a freeze-dryer.

The metal recovering unit is, for example, a unit for decomposing the second chelating agent in the second complex. Examples of the unit include ashers such as a wet asher and a dry asher.

The analyzing unit can be, for example, an optical analyzer, and specific examples thereof include an atomic absorption spectrometer and a visible spectrometer.

The analysis apparatus of the present invention preferably further include a pH measuring unit. The pH measuring unit can be, for example, a pH meter. The analysis apparatus of the present invention preferably includes an introducing unit for introducing a sample, for example. The introducing unit is, for example, preferably a suction-and-discharge unit for sucking and discharging a sample.

According to the analysis apparatus of the present invention, the above-mentioned metal analyzing method of the present invention can be performed. The usage of the analysis apparatus of the present invention is illustrated below. The present invention, however, is by no means limited thereto.

The sample, the first chelating agent, the second chelating agent aqueous solution, and an acidic reagent as a pH adjusting reagent are arranged inside or outside the analysis apparatus.

The pH of the sample is adjusted to acidic conditions (first pH conditions) by adding the acidic reagent to the sample using the acid adding unit. Then, the sample is introduced into the first chelating agent using an introducing unit, and the sample and the chelating agent are mixed using the first mixing unit. Thus, a first mixture is prepared. Thereafter, a first complex in the first mixture is recovered using the complex recovering unit. The second chelating agent aqueous solution is mixed with the recovered first complex using the second mixing unit. Thus, a second mixture is prepared. Then, a liquid fraction containing the second complex dissolved therein in the second mixture is recovered using the liquid fraction recovering unit. The second chelating agent in this liquid fraction is decomposed using the metal recovering unit. Thus a metal is recovered. Then, the recovered metal is analyzed using the analyzing unit. As described above, according to the analysis apparatus of the present invention, the metal analyzing method of the present invention can be performed automatically, for example.

The analysis apparatus of the present invention may further include an output unit for outputting an analysis result with respect to the metal, for example. As the output unit, a monitor or a printer can be used, for example.

EXAMPLES

Next, the examples of the present invention are described. The present invention, however, is by no means limited thereto.

Example A1

(1) Preparation of Urine Sample

Mercury chloride (produced by Wako Pure Chemical Industries, Ltd.) was mixed with pooled urine (pH 6 to 7) collected from a healthy male so as to have a predetermined mercury concentration of 10 μg/L. Thus, an urine sample was obtained. The pH of the urine sample containing the mercury chloride added thereto was 5 to 7. Then, 60 μL of 5N hydrochloric acid (produced by NACALAI TESQUE, INC.) was mixed with 5 mL of the urine sample, so that the pH of the urine sample was adjusted to 1 to 2.

(2) Preparation of First Chelating Agent

Dithizone (produced by Fluka) as a first chelating agent was dissolved in t-butyl alcohol (produced by NACALAI TESQUE, INC.). This solution thus obtained was dispensed in 15 mL-capacity conical tubes made of PP (produced by Nunc) so that the amount of the dithizone in each of the tubes became 1.5 mg. The tubes each containing the solution was then subjected to freeze-drying.

(3) Preparation of Second Chelating Agent Aqueous Solution 1.8 mg of DMSA as a second chelating agent was dissolved in 100 μL each of an aqueous solution and a buffer solution. Thus, DMSA aqueous solutions were prepared. As the aqueous solution, a 100 mmol/L trisodium phosphate aqueous solution (pH 11) was used (hereinafter referred to as a "3Na phosphate aqueous solution"). As the buffer solution, a tris buffer solution (pH 10) was used. The pH of the second chelating agent aqueous solution obtained using the 3Na phosphate aqueous solution was 6, and the pH of the second chelating agent aqueous solution obtained using the tris buffer solution was 4.

(4) Recovery of Mercury from Urine Sample 5 mL of the urine sample was added to each of the tubes each containing the freeze-dried first chelating agent, which was then shaken for 5 minutes at room temperature so as to mix the urine sample and the first chelating agent. Thus, a complex (first complex) between the dithizone and mercury was formed. The tubes were then subjected to centrifugation (19,600 m/s$^2$ (2000×g), 20° C., 10 minutes) so as to separate each of the mixtures into a precipitate containing the first complex and a supernatant. The supernatant was removed, and thereafter the second chelating agent aqueous solutions were added to the respective tubes, which was then shaken for 5 minutes at room temperature so as to mix the precipitate and each of the second chelating agent aqueous solutions. Thus, a complex (second complex) between the mercury and each of the second chelating agents was formed in each of the mixtures. The pH of the mixture obtained using the 3Na phosphate aqueous solution was 6, the pH of the mixture obtained using the tris buffer solution was 4. The tubes were then subjected to centrifugation (19,600 m/s$^2$ (2000×g), 20° C., 10 minutes) so as to separate each of the mixtures into a supernatant containing the second complex dissolved therein and a precipitate. The each supernatant was recovered and used as a mercury-concentrated sample.

The mercury-concentrated samples were subjected to wet ashing. Thus, the second chelating agent in the second complex was decomposed. The wet ashing was performed according to the Mercury Analysis Manual (Ministry of the Environment, March 2004). Then, the mercury concentration of each of the mercury-concentrated samples thus obtained was determined using an atomic absorption spectrometer (trade name: MERCURY ANALYZER, produced by Nippon Instruments, Co., Ltd.). Furthermore, the mercury concentration of each of the urine samples was determined in the same manner as described above using the atomic absorption spectrometer.

Then, the mercury concentration ($X_C$) and volume ($X_V$) of each of the mercury-concentrated samples and the mercury concentration ($Y_C$) and volume ($Y_V$) of each of the urine samples were substituted into the following formula (1). Thus, the recovery rate (%) of mercury was determined. Furthermore, the mercury concentration ($X_C$) of each of the mercury-concentrated samples and the mercury concentration ($Y_C$) of each of the urine samples were substituted into the following formula (2). Thus, the concentration rate (-fold) of mercury was determined.

Recovery rate (%)=100×($X_C$×$X_V$)/($Y_C$×$Y_V$)     (1)

Concentration rate (-fold)=$X_C$/$Y_C$     (2)

The recovery rate and concentration rate of mercury with respect to the urine sample is shown in Table 1 below. As shown in Table 1, mercury could be recovered from the urine sample. From these results, it was found that according to the present invention, mercury could be recovered from the urine sample without requiring the use of an organic medium.

TABLE 1

|  | Mercury-concentrated sample | |
| --- | --- | --- |
|  | 3Na phosphate aqueous solution | Tris buffer solution |
| Recovery rate (%) | 37.68 | 32.75 |
| Concentration rate (−fold) | 18.84 | 16.38 |

Example A2

(1) Preparation of Urine Sample

Urine samples each with the mercury concentration of 10 μg/L were prepared in the same manner as in Example A1. 5N hydrochloric acid (produced by NACALAI TESQUE, INC.) or 5N sodium hydroxide (produced by NACALAI TESQUE, INC.) was added to 5 mL each of the urine samples so that the pH's of the respective urine samples were adjusted to 2, 3, 4, 6.8, and 8. Furthermore, as negative controls, five types of distilled waters with the respective pH's of 2, 3, 4, 6.8, and 8 were used. For the adjustment of the pH's of the distilled waters, 5N hydrochloric acid (produced by NACALAI TESQUE, INC.) or 5N sodium hydroxide (produced by NACALAI TESQUE, INC.) was used as in the adjustment of the pH's of the urine samples.

(2) Preparation of First Chelating Agent

Dithizone was freeze-dried in the same manner as in Example A1.

(3) Preparation of Second Chelating Agent

A second chelating agent aqueous solution was prepared using DMSA and a 3Na phosphate aqueous solution in the same manner as in Example A1.

(4) Recovery of Mercury from Urine Sample

Mercury-concentrated samples were prepared in the same manner as in Example A1. Then, the mercury-concentrated samples were subjected to ashing, and thereafter mercury in each of the mercury-concentrated samples thus obtained was qualitatively determined using an atomic absorption spectrometer.

The results of these are shown in Table 2 below. Mercury was not detected in any of the negative controls (−). In contrast, mercury was detected in all of the mercury-concentrated samples obtained through the formation of the first complex under the respective pH conditions (pH 2 to 8) and the formation of the second complex at pH 6 (+). From these results, it was found that mercury was recovered from the urine sample without requiring the use of an organic medium in the case where the first complex was formed in the wide pH range from 2 to 8, and the second complex was formed at pH 6.

TABLE 2

| pH at the time of forming first complex | Determination |
| --- | --- |
| 2 | + |
| 3 | + |
| 4 | + |
| 6.8 | + |
| 8 | + |
| Control | − |

+: Mercury could be detected.
−: Mercury could not be detected.

Example B1

(1) Preparation of Urine Sample

A urine sample was prepared in the same manner as in Example A1 except that the mercury concentration was set to 80 μg/L, and the pH of the urine sample was adjusted to 1 to 2.

(2) Preparation of First Chelating Agent

Tubes each containing dithizone (produced by Fluka) as a first chelating agent were subjected to freeze-drying in the same manner as in Example A1.

(3) Preparation of Second Chelating Agent Aqueous Solution

Thiopronine (produced by KANTO CHEMICAL CO., INC.) as a second chelating agent was dissolved in 0.1 mol/L nitric acid aqueous solution so as to have the thiropronine concentrations from 100 to 1000 mmol/L. Thus, second chelating agent aqueous solutions were prepared. The pH's of the second chelating aqueous solutions were 1.

(4) Recovery of Mercury from Urine Sample

Mercury-concentrated samples were prepared in the same manner as in Example A1 except that the above-mentioned freeze-dried first chelating agent and the above-mentioned second chelating agent aqueous solutions were used. Then, the mercury-concentrated samples were treated in the same manner as in Example A1, and the mercury concentration of each of the mercury-concentrated samples thus obtained was determined. Furthermore, the mercury concentration of the urine sample was determined in the same manner as in Example A1 using an atomic absorption spectrometer. Then, the recovery rate and concentration rate of mercury were determined in the same manner as in Example A1.

The recovery rate and concentration rate of mercury with respect to the urine sample are shown in Table 3 below. As shown in Table 3, mercury could be recovered from the urine sample and concentrated to about 14- to 27-fold. From these results, it was found that according to the present invention, mercury could be recovered and concentrated from the urine sample without requiring the use of an organic medium.

TABLE 3

| | | Thiopronine concentration (mM) | | | | |
| --- | --- | --- | --- | --- | --- | --- |
| | | 100 | 200 | 500 | 750 | 1000 |
| Mercury concentration (μg/L) | before concentration | 84.66 | 84.66 | 84.66 | 84.66 | 84.66 |
| | after concentration | 1217.84 | 1499.74 | 2009.84 | 2287.17 | 2215.10 |
| Recovery rate (%) | | 28.77 | 35.43 | 47.48 | 54.03 | 52.33 |
| Concentration rate (−fold) | | 14.39 | 17.72 | 23.74 | 27.02 | 26.17 |

Example B2

A second chelating agent aqueous solution was prepared using DMPS (produced by Tokyo Chemical Industry Co., Ltd.) as a second chelating agent as substitute for thiopronine. The pH of the second chelating agent aqueous solution was 1. Mercury was recovered from an urine sample in the same manner as in Example B1 for using the above-described second chelating agent aqueous solution. The results are shown in Table 4 below. As shown in Table 4, mercury could be recovered from the urine sample and concentrated to about 18- to 37-fold. From these results, it was found that according to the present invention, mercury could be recovered and concentrated from the urine sample without requiring the use of an organic medium.

TABLE 4

| | | DMPS concentration (mM) | | | | |
| --- | --- | --- | --- | --- | --- | --- |
| | | 100 | 200 | 500 | 750 | 1000 |
| Mercury concentration (μg/L) | before concentration | 84.87 | 84.87 | 84.87 | 84.87 | 84.87 |
| | after concentration | 1496.80 | 2125.91 | 2685.18 | 3113.06 | 3016.25 |

TABLE 4-continued

| | DMPS concentration (mM) | | | | |
| --- | --- | --- | --- | --- | --- |
| | 100 | 200 | 500 | 750 | 1000 |
| Recovery rate (%) | 35.27 | 50.10 | 63.27 | 73.36 | 71.08 |
| Concentration rate (-fold) | 17.64 | 25.05 | 31.64 | 36.68 | 35.54 |

Example B3

L-cysteine (produced by NACALAI TESQUE, INC.) was used as a second chelating agent as substitute for thiopronine. The L-cysteine was dissolved in 0.1 mol/L nitric acid aqueous solution so as to have the L-cysteine concentrations from 200 to 1000 mmol/L. Thus, the second chelating agent aqueous solution was prepared. The pH of the second chelating agent aqueous solution was 1. Mercury was recovered from an urine sample in the same manner as in Example B1 except for using the above-described second chelating agent aqueous solution. The results are shown in Table 5 below. As shown in Table 5, mercury could be recovered from the urine sample and concentrated to about 12- to 15-fold. From these results, it was found that according to the present invention, mercury could be recovered and concentrated from the urine sample without requiring the use of an organic medium.

TABLE 5

| | | L-cysteine concentration (mM) | | | |
| --- | --- | --- | --- | --- | --- |
| | | 200 | 500 | 750 | 1000 |
| Mercury concentration (µg/L) | before concentration | 84.87 | 84.66 | 84.87 | 84.87 |
| | after concentration | 1038.45 | 1237.46 | 1200.73 | 1080.51 |
| Recovery rate (%) | | 24.47 | 29.24 | 28.29 | 25.46 |
| Concentration rate (-fold) | | 12.24 | 14.62 | 14.15 | 12.73 |

Example C1

(1) Preparation of Urine Sample

An urine sample was prepared in the same manner as in Example A1, and the pH of the urine sample was adjusted to about 1 to 2.

(2) Preparation of First Chelating Agent

Tubes each containing dithizone (produced by Fluka) as a first chelating agent were subjected to freeze-drying in the same manner as in Example A1.

(3) Preparation of Second Chelating Agent Aqueous Solution

Sodium thiosalicylate (produced by Tokyo Chemical Industry Co., Ltd.) as a second chelating agent was dissolved in a 0.1 mol/L nitric acid aqueous solution so as to have the sodium thiosalicylate concentration of 500 mmol/L. Thereafter, the sodium thiosalicylate was dissolved using 5N NaOH. Thus, a second chelating agent aqueous solution was prepared. The pH of the second chelating agent aqueous solution was 4.

(4) Recovery of Mercury from Urine Sample

Mercury-concentrated samples were prepared in the same manner as in Example A1 except that the above-mentioned freeze-dried first chelating agent and the above-mentioned second chelating agent aqueous solution were used. Then, the mercury-concentrated samples were treated in the same manner as in Example A1, and the mercury concentration of each of the mercury-concentrated samples thus obtained was determined. Then, the mercury-concentrated samples were treated in the same manner as in Example A1, and the mercury concentration of each of the mercury-concentrated samples thus obtained was determined. Furthermore, the mercury concentration of the urine sample was determined in the same manner as in Example A1 using an atomic absorption spectrometer. Then, the recovery rate and concentration rate of mercury were determined in the same manner as in Example A1.

The recovery rate and concentration rate of mercury with respect to the urine sample are shown in Table 6 below. As shown in Table 6, mercury was recovered from the urine sample and concentrated, using the first chelating agent and the second chelating agent. From these results, it was found that according to the present invention, mercury could be recovered and concentrated from the urine sample without requiring the use of an organic medium.

TABLE 6

| | | Sodium thiosalicylate |
| --- | --- | --- |
| Mercury concentration (µg/L) | before concentration | 9.37 |
| | after concentration | 121.03 |
| Recovery rate (%) | | 25.84 |
| Concentration rate (-fold) | | 12.92 |

Example D1

(1) Preparation of Urine Sample

An urine sample (pH 6 to 7) was prepared, and the pH of the urine sample was adjusted to 1 to 2, in the same manner as in Example A1.

(2) Preparation of First Chelating Agent

The predetermined amounts (1.5, 34.5, and 7.5 mg) of glyoxaldithiosemicarbazone (produced by Wako Pure Chemical Industries, Ltd.) as a first chelating agent were weighted into the respective 15 mL-capacity conical tubes made of polypropylene (PP) (produced by Nunc).

(3) Preparation of Second Chelating Agent Aqueous Solution

Thiopronine (produced by KANTO CHEMICAL CO., INC.) was dissolved in a 0.1 mol/L nitric acid aqueous solution so as to have the thiopronine concentration of 500 mmol/L. Thus, a second chelating agent aqueous solution was prepared. The pH of the second chelating agent aqueous solution was 1.

(4) Recovery of Mercury from Urine Sample

The whole amount of the urine sample was added to each of the tubes each containing the first chelating agent, which was then shaken for 5 minutes at room temperature so as to mix the urine sample and the first chelating agent. A complex (first complex) between the first chelating agent and mercury was formed. After forming the first complex, mercury-concentrated samples were prepared in the same manner as in Example A1 except that the above-mentioned second chelating agent aqueous solution was used.

Then, the mercury-concentrated samples were treated in the same manner as in Example A1, and the mercury concentration of each of the mercury-concentrated samples thus obtained was determined. Furthermore, the mercury concentration of the urine sample was determined in the same manner as in Example A1 using an atomic absorption spectrometer. Then, the recovery rate and concentration of mercury were determined in the same manner as in Example A1.

The recovery rate and concentration rate of mercury with respect to the urine sample are shown in Table 7 below. As shown in Table 7, mercury could be recovered from the urine samples and concentrated to about 19- to 36-fold. From these results, it was found the according to the present invention, mercury could be recovered and concentrated from the urine samples without requiring the use of an organic medium.

TABLE 7

| | | Amount of glyoxaldithiosemicarbazone (mg) | | | |
|---|---|---|---|---|---|
| | | 1.5 | 3 | 4.5 | 7.5 |
| Mercury concentration (μg/L) | before concentration | 9.81 | 9.81 | 9.81 | 11.07 |
| | after concentration | 189.05 | 247.23 | 250.81 | 396.40 |
| Recovery rate (%) | | 38.52 | 50.38 | 51.11 | 71.61 |
| Concentration rate (−fold) | | 19.26 | 25.19 | 25.55 | 35.81 |

Example D2

7.5 mg of glyoxaldithiosemicarbazone (produced by Wako Pure Chemical Industries, Ltd.) was used as a first chelating agent, and DMSA, DMPS, L-cysteine, and sodium thiosalicylate were used as second chelating agents. Mercury was recovered from an urine sample in the same manner as in Example D1 except that these chelating agents were used.

(1) Preparation of Second Chelating Agent Aqueous Solution (1-1) Preparation of DMSA Aqueous Solution DMSA was mixed with a 0.1 mol/L nitric acid aqueous solution, and then, 5N NaOH was added thereto so as to dissolve the DMSA. A 0.1 mol/L nitric acid aqueous solution was added to his aqueous solution thus obtained so as to have the DMSA concentration of 500 mmol/L. Thus, a DMSA aqueous solution was prepared. The pH of the DMSA aqueous solution was 4.

(1-2) Preparation of DMPS Aqueous Solution

DMPS was dissolved in a 0.1 mol/L nitric acid aqueous solution so as to have the DMPS concentration of 500 mmol/L. Thus, a DMPS aqueous solution was prepared. The pH of the DMPS aqueous solution was 4.

(1-3) Preparation of L-Cysteine Aqueous Solution

L-cysteine was dissolved in 0.1 mol/L nitric acid aqueous solution so as to have the L-cysteine concentration of 500 mmol/L. Thus, an L-cysteine aqueous solution was prepared. The pH of the L-cysteine aqueous solution was 1.

(1-4) Preparation of Na Thiosalicylate Aqueous Solution

Na thiosalicylate was mixed with a 0.1 mol/L nitric acid aqueous solution, and further 5N NaOH was added thereto, so as to dissolve the Na thiosalicylate. A 0.1 mol/L nitric acid aqueous solution was added to this aqueous solution thus obtained so as to have the Na thiosalicylate concentration of 500 mmol/L. Thus, a Na thiosalicylate aqueous solution was prepared. The pH of the Na thiosalicylate aqueous solution was 4.

The recovery rate and concentration rate of mercury with respect to the urine sample are shown in Table 8 below. As shown in Table 8, mercury could be recovered from the urine sample and concentrated. From these results, it was found that according to the present invention, mercury could be recovered from the urine sample and concentrated without requiring the use of an organic medium.

TABLE 8

| | | Second chelating agent | | | |
|---|---|---|---|---|---|
| | | DMSA | DMPS | L-cysteine | Na thiosalicylate |
| Mercury concentration (μg/L) | before concentration | 11.07 | 11.07 | 11.07 | 11.07 |
| | after concentration | 367.36 | 378.25 | 390.96 | 333.96 |
| Recovery rate (%) | | 66.37 | 68.34 | 70.63 | 60.33 |
| Concentration rate (−fold) | | 33.18 | 34.17 | 35.32 | 30.17 |

Example E1

Lead was recovered from a liquid sample containing lead, using a chelating agent.

(1) Preparation of Liquid Sample

A 0.34 mol/L sodium chloride aqueous solution containing 0.01% poly(oxyethylene)sorbitan monolaurate (Tween-20) was prepared. A lead standard solution (produced by Wako Pure Chemical Industries, Ltd.) was added to the aqueous solution thus obtained so as to have the lead concentration of 0.5 mg/L. Thus, a liquid sample was prepared. On the other hand, a control sample (with the leas concentration of 0 mg/L) was prepared by adding a 0.1 mol/L nitric acid aqueous solution as substitute for the lead standard solution. The pH's of the liquid sample and the control sample were 6.

(2) Preparation of First Chelating Agent

Dithizone (produced by Fluka) was dissolved in t-butyl alcohol (produced by NACALAI TESQUE, INC.). This solution thus obtained was dispensed in 1 mL-capacity tubes made of PP (produced by produced by Nichiryo Co., Ltd.) so that the amount of the dithizone in each of the tubes became 1.5 mg. The tubes each containing the solution were then subjected to freeze-drying.

(3) Recovery of Lead from Liquid Sample 1 mL of the liquid sample was added to one of the tubes, which was then shaken for 5 minutes at room temperature so as to mix the liquid sample and the dithizone. Thereafter, the tube was stood still for 2 hours, so that a complex between the dithizone and lead was formed. The tube was then subjected to centrifugation (19,600 m/s$^2$ (2000×g), 20° C., 10 minutes) so as to separate the mixture into a precipitate containing the complex and a supernatant. The supernatant was removed, and thereafter 0.1 mL of a 0.1 mol/L nitric acid aqueous solution was added to the tube. Under the same conditions as mentioned above, the precipitate and the nitric acid aqueous solution were mixed in the tube, and then the tube was subjected to centrifugation so as to separate the mixture into a precipitate containing the complex and a supernatant. Then, the supernatant was removed, and thereafter 0.1 mL of a 0.4N NaOH aqueous solution (pH 12) was added to the tube, which was then repeatedly turning upside down so as to mix the precipitate and the NaOH aqueous solution. Thus, the complex in the precipitate was dissolved. An aqueous solution (pH 12) containing the complex dissolved therein was used as a lead-concentrated sample.

The lead-concentrated sample was subjected to wet ashing. Thus, the dithizone in the complex was decomposed. Then, the lead concentration of the lead-concentrated sample thus obtained was determined by mass spectrometry using an ICP mass spectrometer (ICP-MS, trade name: ICPM-8500, produced by Shimadzu Corporation). Furthermore, the lead concentration of the control sample was determined in the same manner as described above.

Then, the lead concentration ($X_C$) and volume ($X_V$) of the lead-concentrated sample and the lead concentration ($Y_C$) and volume ($Y_V$) of the liquid sample were substituted into the following formula (3). Thus, the recovery rate (%) of lead was determined. Furthermore, the lead concentration ($X_C$) of the lead-concentrated sample and the lead concentration ($Y_C$) of the liquid sample were substituted into the following formula (4). Thus, the concentration rate (-fold) of lead was determined.

$$\text{Recovery rate (\%)} = 100 \times (X_C \times X_V)/(Y_C \times Y_V) \quad (3)$$

$$\text{Concentration rate (-fold)} = X_C/Y_C \quad (4)$$

The recovery rate and concentration rate of lead with respect to the liquid sample (with the lead concentration of 0.5 mg/L) and control sample (with the lead concentration of 0 mg/L) is shown in Table 9 below. It was found from the results shown in Table 9, that a complex between lead and the first chelating agent was formed, so that the complex containing lead could be recovered from the liquid sample. Therefore, it is obvious that a second complex is formed by causing the complex between the first chelating agent and lead to react with a second chelating agent, and lead can be recovered from the second complex. Thus, it was found that according to the present invention, not only mercury but also the other metals such as lead and the like can be recovered.

TABLE 9

|  |  | Lead concentration of liquid sample (mg/L) | |
|---|---|---|---|
|  |  | 0 | 0.5 |
| Lead concentration (mg/L) | before concentration | −0.02 | 0.49 |
|  | after concentration | 0.01 | 1.04 |
| Recovery rate (%) |  | — | 21.03 |
| Concentration rate (−fold) |  | — | 2.10 |

As described above, according to the present invention, a metal can be recovered easily by utilizing the difference in solubility between the first chelating agent and the second chelating agent in an aqueous medium without substantially using an organic medium. Therefore, the present invention is really useful in critical examinations of samples derived from biological bodies and environmental testing, for example.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A method for recovering a metal, the method comprising the steps of:
    forming a first complex between a first chelating agent and a metal present in a sample in a first mixture prepared by mixing the first chelating agent and the sample;
    recovering the first complex from the first mixture;
    forming a second complex between the metal derived from the first complex and a second chelating agent in a second mixture prepared by mixing the first complex and an aqueous medium comprising the second chelating agent; and
    recovering the metal by recovering a liquid fraction containing the second complex dissolved therein from the second mixture, wherein
    in the step of forming a first complex, the first mixture is prepared under pH conditions where the first chelating agent is dissolved or partially dissolved in the first mixture, and
    in the step of forming a second complex, the aqueous medium of the second chelating agent is under pH conditions where the first chelating agent is insoluble therein.

2. The method according to claim 1, wherein the first chelating agent comprises a sulfur-containing group.

3. The method according to claim 1, wherein the first chelating agent is at least one selected from the group consisting of a thiocarbazone group, a thiosemicarbazone group, a thiocarbadiazone group, a thiourea group, a thiosemicarbazide group, and a rubeamate group.

4. The method according to claim 1, wherein the first chelating agent is at least one selected from the group consisting of 1,5-diphenyl-3-thiocarbazone, glyoxaldithiosemicarbazone, and (1E,2E)-aminocarbothioyl hydrazono phenylethanal thiosemicarbazone.

5. The method according to claim 1, wherein the second chelating agent comprises a thiol group.

6. The method according to claim 1, wherein the second chelating agent comprises a structure represented by at least one selected from the group consisting of structural formulae (3), (4), and (5):

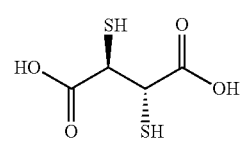

(3)

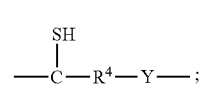

(4)

where in the structural formula (4),
R$^4$ represents an alkyl group or an amino alkyl group each with a carbon number of 1 or 2 or is not present, and
Y represents

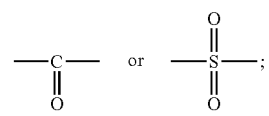

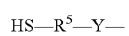

(5)

where in the structural formula (5),
R$^5$ represents an aromatic hydrocarbon group, and Y represents

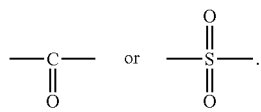

7. The method according to claim 3, wherein the second chelating agent is at least one selected from the group consisting of meso-2,3-dimercapto succinic acid, N-(2-mercaptopropionyl)glycine, 1,2-dimercapto-1-sodium propanesulfonate, cysteine, thiosalicylic acid, and sodium thiosalicylate.

8. The method according to claim 1, where in the step of forming a first complex, the pH conditions where the first chelating agent is dissolved or partially dissolved in the first mixture are about pH 8 or less.

9. The method according to claim 7, where in the step of forming a first complex, the pH conditions where the first chelating agent is dissolved or partially dissolved in the first mixture are about pH 4 or less.

10. The method according to claim 1, where in the step of forming a second complex, the pH conditions where the first chelating agent is dissolved or partially dissolved in the first mixture are about pH 6.8 or less.

11. The method according to claim 1, wherein the metal is at least one selected from the group consisting of Bi, Hg, Cd, Pd, Zn, TI, Ag, Pb, and As.

* * * * *